(12) United States Patent
Trievel et al.

(10) Patent No.: US 7,504,234 B2
(45) Date of Patent: Mar. 17, 2009

(54) ASSAYS FOR S-ADENOSYLMETHIONINE (ADOMET)-DEPENDENT METHYLTRANSFERASE ACTIVITY

(75) Inventors: Raymond Trievel, Ypsilanti, MI (US); Evys Collazo-Santiago, Ann Arbor, MI (US); Jean-Francois Couture, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 111 days.

(21) Appl. No.: 11/389,393

(22) Filed: Mar. 24, 2006

(65) Prior Publication Data

US 2007/0224655 A1    Sep. 27, 2007

(51) Int. Cl.
*C12Q 1/34*    (2006.01)
(52) U.S. Cl. .......................................... 435/18; 435/15
(58) Field of Classification Search .................... 435/18, 435/15
See application file for complete search history.

(56) References Cited

U.S. PATENT DOCUMENTS

| | | | |
|---|---|---|---|
| 6,063,581 A * | 5/2000 | Sundrehagen | 435/7.1 |
| 6,376,210 B1 * | 4/2002 | Yuan | 435/18 |
| 6,610,504 B1 * | 8/2003 | Yuan | 506/11 |
| 6,713,273 B2 * | 3/2004 | Xu et al. | 435/15 |
| 7,192,729 B2 * | 3/2007 | Yuan | 435/18 |
| 2005/0244912 A1 * | 11/2005 | Yuan et al. | 435/18 |

FOREIGN PATENT DOCUMENTS

WO    WO 2007/087541 A2 *    8/2007

OTHER PUBLICATIONS

Trievel R. et al. Application of a Fluorescent Histone Acetyltransferase Assay to Probe the substrate Specificity of the Human p300/CBP Associated Factor. Analytical Biochemistry 287 319-328, 2000.*
Wright S. et al. Evaluation of Methods for the Quantitation of Cysteines in Proteins. Analytical Biochemistry 265 8-14, 1998.*
Graves, T. et al. A Universal Competitive Fluorescence Polarization Activity Assay for S-Adenosylmethionine Utilizing Methyltransferases. Analyical Biochemistry 373(2)296-306, 2008.*
Chirpich, T.P., "Lysine 2,3-Aminomutase," The Journal of Biological Chemistry, vol. 245, No. 7, Apr. 10, 1970, pp. 1778-1789.
Couture, Jean-Francois, "Structural basis for the methylation site specificity of SET7/9," Nature Structural & Molecular Biology, vol. 13, No. 2, Feb. 2006, pp. 140-146.
Eskeland, R., "The N-Terminus of Drosophila SU(VAR)3-9 Mediates Dimerization and Regulates Its Methyltransferase Activity," Biochemistry 2004, 43, pp. 3740-3749.
Giannattasio, M., "The DNA Damage Checkpoint Response Requires Histone H2B Ubiquitination by Rad6-Bre1 and H3 Methylation by Dot1," The Journal of Biological Chemistry, vol. 280, No. 11, Mar. 18, 2005, pp. 9879-9886.
Hermann, A., "Biochemistry and biology of mammalian DNA methyltransferases," CMLS, Cell. Mol. Life Sci. 61 (2004) pp. 2571-2587.
Hess, Jay L., "MLL: a histone methyltransferase disrupted in leukemia," Trends in Molecular Medicine, vol. 10, No. 10, Oct. 2004, pp. 500-507.
Kim, Keun-Cheol, "Inactivation of a Histone Methyltransferase by Mutation in Human Cancers," Cancer Research 63 pp. 7619-7623, Nov. 15, 2003.
Kleer, Celina G., "EZH2 is a marker of aggressive breast cancer and promotes neoplastic transformation of breast epithelial cells," PNAS, vol. 100, No. 20, Sep. 30, 2003, pp. 11606-11611.
Kloor, Dorris, et al., "S-Adenosylhomocysteine hydrolase as a target for intracellular adenosine action," Trends in Pharmacological Sciences, vol. 25, No. 6, Jun. 2004.
Kuzmichev, A., "Different Ezh2-Containing Complexes Target Methylation of Histone H1 or Nucleosomal Hisone H3," Molecular Cell, vol. 14, pp. 183-193, Apr. 23, 2004.
Langmuir, Margaret E., et al., "New Napthopyranone Based Fluorescent Thiol Probes," Tetrahedron Letters, vol. 36, No. 23, pp. 3989-3992, 1995.
Marmorstein, R., "Structure of Histone Acetyltransferases," J. Mol. Biol. (2001) 311, pp. 433-444.
Nishioka, K., "Methods and tips for the purification of human histone methyltransferases," Methods, 31 (2003), pp. 49-58.
Patnaik, D., "Substrate Specificity and Kinetic Mechanism of Mammalian G9a Histone H3 Methyltransferase," The Journal of Biological Chemistry, vol. 279, No. 51, Dec. 14, 2004, pp. 53248-53258.
Porcelli, M., et al., "Expression, Purification, and Characterization of Recombinant S-Adenosylhomocysteine Hydrolase from the Thermophilic Archaeon Sulfolobus solfataricus", Protein Expression and Purification, 18, pp. 27-35 (2000).

(Continued)

*Primary Examiner*—Ralph Gitomer
(74) *Attorney, Agent, or Firm*—Casimir Jones, S.C.

(57) ABSTRACT

The present invention relates to coupled enzyme assays. In particular, the present invention provides a coupled fluorescent assay for detection of S-adenosylmethionine (AdoMet)-dependent methyltransferase activity and S-adenosylhomocysteine hydrolase enzyme activity.

13 Claims, 4 Drawing Sheets

OTHER PUBLICATIONS

Porcelli, M., et al., "S-Adenosylhomocysteine hydrolase from the thermophilic archaeon Sulfolobus solfatarius: purification, physico-chemical and immunological properties," Biochimica et Biophysica cta, 1164 (1993) pp. 179-188.

Sanders, Steven L., "Methylation of Histone H4 Lysine 20 Controls Recruitment of Crb2 to Sites of DNA Damage," Cell, vol. 119, 603-614, Nov. 24, 2004.

Schneider, R., "Unsafe SETs: histone lysine methyltransferases and cancer," Trends in Biochemical Sciences, vol. 27, No. 8, Aug. 2002, pp. 396-402.

Sellers, William R., "The EZH2 polycomb transcriptional repressor—a marker or mover of metastatic prostate cancer," Cancer Cell: Nov. 2002, pp. 349-350.

Sheffeld, Peter, "Overcoming Expression and Purification Problems of RhoGDI Using a Family of 'Parallel' Expression Vectors," Protein Expression and Purification, 15, pp. 34-39 (1999).

Sims, R., "Histone lysine methylation: a signature for chromatin function," Trends in Genetics, vol. 19 No. 11, Nov. 2003, pp. 629-639.

Tachibana, Makoto, SET Domain-containing Protein, G9a, Is a Novel Lysine-preferring Mammalian Histone Methyltransferase with Hyperactivity and Specific Selectivity to Lysines 9 and 27 of Histone H3, Journal of Biological Chemisty, vol. 276, No. 27, Jul. 6, 2001, pp. 25309-25317.

Trievel, R., "Structure and Function of Histone Methyltransferases," Critical Reviews in Eukaryotic Gene Expression, 14(3):147-169 (2004).

Trievel, Raymond C., "Application of a Fluorescent Histone Acetyltransferase Assay to Probe the Substrate Specificity of the Human p300/CBP-Associated Factor,"Analytical Biochemistry 287, pp. 319-328 (2000).

Trievel, Raymond C., "Structure and a Catalytic Mechanism of a SET Domain Protein Methyltransferase," Cell, vol. 111, pp. 91-103, Oct. 4, 2002.

Varambally, S., et al., "The polycomb group protein EZH2 is involved in progression of prostate cancer," Nature, vol. 419, Oct. 10, 2002, pp. 624-629.

Wang, C., et al., "A general fluorescence-based coupled assay for S-adenosylmethionine-dependent methyltransferases," Biochemical and Biophysical Research Communications 331 (2005), pp. 351-356.

Wright, S. Kirk, et al., Evaluation of Methods for the Quantitation of Cysteines in Proteins, Analytical Biochemistry 265, pp. 8-14 (1998).

Yuan, Chong-Sheng, "Mechanism of Inactivation of S-Adenosylhomocysteine Hydrolase by (Z)-4',5'-Didehydro-5'-Deoxy-5'-Fluoroadenosine," Journal of Biological Chemmistry, vol. 268, No. 23, Aug. 15, 1993, pp. 17030-17037.

Wang, C., et al., "A general fluorescence-based coupled assay for S-adenosylmethionine-dependent methyltransferases," Biochemical and Biophysical Research Communications 331 (2005), pp. 351-356.

\* cited by examiner

ThioGlo 1

$Ex_{max}$ = 384 nm $Em_{max}$ = 513 nm

ASSAYS FOR S-ADENOSYLMETHIONINE (ADOMET)-DEPENDENT METHYLTRANSFERASE ACTIVITY

FIELD OF THE INVENTION

The present invention relates to coupled enzyme assays. In particular, the present invention provides a coupled fluorescent assay for detection of S-adenosylmethionine (AdoMet)-dependent methyltransferase activity.

BACKGROUND OF THE INVENTION

Methylation is a common covalent modification of biological small molecules, nucleic acids, and proteins. Methylation is a prominent posttranslational modification in intracellular signaling pathways. In eukaryotes, genomic DNA and histones that comprise chromatin are subject to this modification. Methylation of cytosine bases in CpG dinucleotide repeats is enriched in transcriptionally repressed chromatin and mediates epigenetic silencing within these domains (Hermann et al., Cell Mol. Life Sci. 61 (2004) 2571-2587). Histones H3 and H4, which constitute part of the histone octamer in the nucleosome core particle, undergo methylation at distinct arginine and lysine residues (Trievel, Crit. Rev. Eukaryot. Gene Expr. 14 (2004) 147-170). In addition, linker histone H1b, which binds to the exterior of the nucleosome, is subject to methylation at Lys-26 (Kuzmichev et al., Mol. Cell 14 (2004) 183-193).

Efforts by numerous groups have identified many of the enzymes that methylate DNA and histones in chromatin. These enzymes all share a common mechanistic feature in that they utilize S-adenosylmethionine (AdoMet) as the methyl-donating cofactor. The enzymes that catalyze methylation of CpG repeats are generally known as DNA methyltransferases or DNMTS (Herman et al., supra), while the enzymes that methylate arginines and lysines in histones are collectively referred to as histone methyltransferases (HMTs). HMTs can be further classified based on their amino acid specificity: protein arginine methyltransferases (PRMTs) and histone lysine methyltransferases (HKMTs) (Trievel, 2004, supra). Methylation of specific arginines and lysines within core and linker histones by HMTs has been directly linked to transcriptional regulation. For example, methylation of Lys-4 in histone H3 is enriched in transcriptionally active loci, whereas H3 Lys-9 methylation is a hallmark of heterochromatin and silent euchromatin (Sims et al., Trends Genet. 19 (2003) 629-639). Moreover, several HKMTs have recently been implicated in DNA repair checkpoints in the cell cycle (Sanders et al., Cell 119 (2004) 603-614; Giannattasio et al., J. Biol. Chem. (2005)), suggesting that these enzymes may have broader roles in chromatin remodeling than previously believed.

Elucidating the determinants of the substrate specificity of HMTs is pivotal to understanding the biological functions of these enzymes. Unlike histone acetyltransferases (HATs), which are generally promiscuous with regard to their substrate specificity (Marmorstein, J. Mol. Biol. 311 (2001) 433-444), most HMTs are highly selective and site-specifically methylate discrete residues within histones. This selectivity is exemplified by HKMTs, many of which modify only individual lysyl residues within histones H1b, H3, or H4 (Trievel, 2004, supra, Kuzmichev et al., supra). To characterize the substrate specificities of these enzymes, radioactive methyltransferase assays, which measure the incorporation of tritiated methyl groups from radiolabeled AdoMet into protein or peptide substrates, have been used to determine sites of lysine methylation within histones and other nuclear proteins (Nishioka et al., Methods 31 (2003) 49-58). The steady state kinetic parameters of several HMTs have been quantitatively measured using this technique, including the human histone H3 Lys-4-specific methyltransferase SET7/9 (Trievel et al., Cell 111 (2002) 91-103) and the H3 Lys-9-specific enzymes mouse ESET (Wang et al., Mol. Cell 12 (2003) 475-487), *Drosophila* SU(VAR)3-9 (Eskeland et al., Biochemistry 43 (2004) 3740-3749), and mouse G9A (Patnaik et al., J Biol. Chem. (2004)). Although highly sensitive, the radiometric assay is laborious and not suited to high-throughput applications. Furthermore, the accumulation of AdoHcy during this assay can result in significant product inhibition of HMTs (Patnaik et al., supra, Kim et al., Cancer Res. 63 (2003) 7619-7623) and lead to errors in determining the steady state kinetic parameters of these enzymes.

What is needed are more efficient and accurate assays for HMT activity.

SUMMARY OF THE INVENTION

The present invention relates to coupled enzyme assays. In particular, the present invention provides a coupled fluorescent assay for detection of S-adenosylmethionine (AdoMet)-dependent methyltransferase activity.

Accordingly, in some embodiments, the present invention provides methods for screening modulators (e.g., drugs) of S-adenosylmethionine (AdoMet)-dependent methyltransferase enzymes (e.g., histone, small molecule, DNA, RNA, and protein arginine methyltransferases). The present invention further provides methods of studying S-adenosylmethionine (AdoMet)-dependent methyltransferase enzyme function and structure (e.g., research applications).

For example, in some embodiments, the present invention provides a method, comprising contacting S-adenosylhomocysteine with an S-adenosylhomocysteine hydrolase under conditions such that the S-adenosylhomocysteine hydrolase hydrolyzes the S-adenosylhomocysteine to homocysteine; contacting the homocysteine with a reporter molecule (e.g., a thiol sensitive fluorophore) under conditions such that the reporter molecule is covalently conjugated to the homocysteine to form a labeled homocysteine; and measuring the concentration of the labeled homocysteine.

The present invention is not limited to a particular type of reporter molecule. In some embodiments, the reporter molecule is selected from, for example, phosphorescent reporter molecules, fluorescent reporter molecules (e.g., thiol sensitive fluorophores), chemoluminescent reporter molecules, colloidal metal reporting molecules, bioluminescent reporter molecules, radioisotope reporter molecules, phosphorescent reporter molecules, and colorimetric reporter molecules. In some embodiments, the thiol sensitive fluorophore is Thio-Glo 1. In some embodiments, the S-adenosylhomocysteine hydrolase enzyme is *S. solfataricus* S-adenosylhomocysteine hydrolase. In some embodiments, the S-adenosylhomocysteine is the product of a S-adenosylmethionine (AdoMet)-dependent methyltransferase (e.g., histone methyl transferase) reaction.

The present invention further provides a method, comprising: contacting a S-adenosylmethionine (AdoMet)-dependent methyltransferase enzyme (e.g., histone methyl transferase enzyme) with a substrate for the S-adenosylmethionine (AdoMet)-dependent methyltransferase enzyme (e.g., histone methyl transferase enzyme) under conditions such that S-adenosyl-homocysteine is generated; contacting the S-adenosyl-homocysteine with a S-adenosylhomocysteine hydrolase enzyme under conditions such that the S-adenosylhomocysteine hydrolase hydrolyzes the S-adenosylhomocysteine to homocysteine; contacting the homocysteine with the thiol sensitive fluorophore under conditions such that the thiol sensitive fluorophore is covalently conjugated to the homocysteine to form a labeled homocysteine; and measuring the concentration of the labeled homocysteine. In some embodiments, the method further comprises the step of contacting the S-adenosylmethionine (AdoMet)-dependent methyltransferase enzyme (e.g., histone methyl transferase enzyme) and the substrate with a test compound (e.g., a drug). In some embodiments, the concentration of labeled homocysteine is altered in the presence of the test compound relative to the level in the absence of the test compound. In some preferred embodiments, the method is a high throughput screening method. In some embodiments, the thiol sensitive fluorophore is ThioGlo 1. In some embodiments, the S-adenosylhomocysteine hydrolase enzyme is *S. solfataricus* S-adenosylhomocysteine hydrolase.

The present invention additionally provides a kit for the detection of the product of a S-adenosylmethionine (AdoMet)-dependent methyltransferase enzyme (e.g., histone methyl transferase enzyme) reaction, comprising: an S-adenosylhomocysteine hydrolase enzyme; and a thiol sensitive fluorophore. In some embodiments, the thiol sensitive fluorophore is ThioGlo 1. In some embodiments, the S-adenosylhomocysteine hydrolase enzyme is *S. solfataricus* S-adenosylhomocysteine hydrolase.

Other embodiments of the invention are described in the description and examples below.

DEFINITIONS

Figure 1:
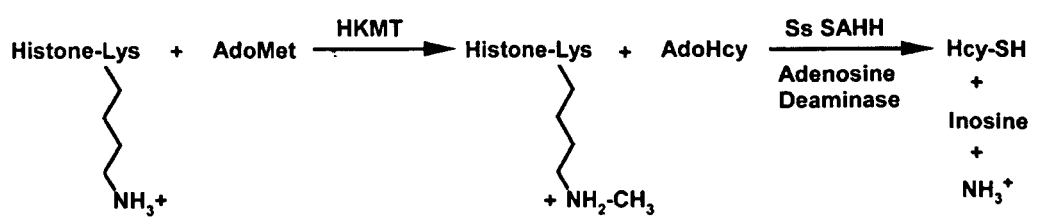
FIG. 1 shows the coupled fluorescent HMT assay.
Figure 1:
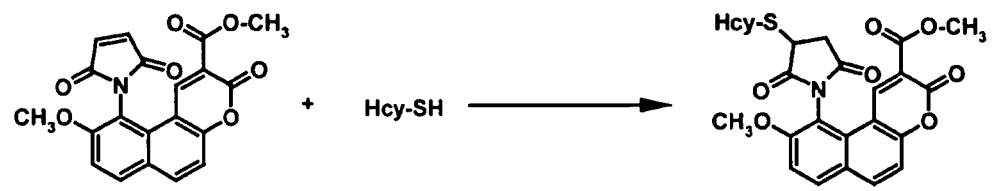

To facilitate understanding of the invention, a number of terms are defined below.

As used herein, the term "host cell" refers to any eukaryotic cell (e.g., mammalian cells, avian cells, amphibian cells, plant cells, fish cells, and insect cells), whether located in vitro or in vivo.

As used herein, the term "mimetic" refers to a small molecule compound that mimics the binding of a ligand to its target.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

As used herein the term, the term "in vitro" refers to an artificial environment and to processes or reactions that occur within an artificial environment. In vitro environments can consist of, but are not limited to, test tubes and cell cultures. The term "in vivo" refers to the natural environment (e.g., an animal or a cell) and to processes or reaction that occur within a natural environment.

As used herein, the term "reporter molecule," refers to an entity used in, for example, detecting assay activity. Examples of "reporter molecules" useful in the present invention include, but are not limited to, phosphorescent reporter molecules, fluorescent reporter molecules (e.g., thiol sensitive fluorophores), chemoluminescent reporter molecules, bioluminescent reporter molecules, radioisotope reporter molecules, phosphorescent reporter molecules, colloidal metals, and colorimetric reporter molecules.

As used herein, the term "response," when used in reference to an assay, refers to the generation of a detectable signal (e.g., accumulation of reporter protein, increase in ion concentration, accumulation of a detectable chemical product).

As used herein, the term "purified" refers to molecules, either nucleic or amino acid sequences that are removed from their natural environment isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated.

The term "test compound" refers to any chemical entity, pharmaceutical, drug, and the like contemplated to be useful in the treatment and/or prevention of a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

DETAILED DESCRIPTION OF THE INVENTION

The present invention relates to coupled enzyme assays. Experiments conducted during the course of development of the present invention provided a coupled-fluorescence based assay for S-adenosylmethionine (AdoMet)-dependent methyltransferases (e.g., histone, small molecule, DNA, RNA, and protein arginine methyltransferases).

S-adenosylmethionine (AdoMet)-dependent methyltransferases are involved in a variety of biological functions. In particular, certain histone methytransferases (HMTs) have been shown to have roles in cancer. The two most prominent cancer-linked HMTs are MLL and EZH2 (See e.g., Kleer et al., PNAS 100:11606 [2003]; Sellers et al., Cancer cell November 2002 pg. 349; Varambally et al., Nature 419:624 [2002]; Hess, Trends in Mol. Med. 10: 500 [2004]; Schneider et al. Trends in Biochem. Sci 27:396 [2002]; each of which is herein incorporated by reference in its entirety). Accordingly, in some embodiments, the present invention provides methods of measuring HMT activity of HMTs involved in cancer (e.g., to identify modulators of such enzymes).

The present invention is illustrated with a histone methyltransferase enzyme. However, the methods of the present invention are suitable for use with any S-adenosylmethionine (AdoMet)-dependent methyltransferase. Additional experiments conducted during the course of development of the present invention utilized the methods of the present invention to study Human SET7/9, a protein lysine methyltransferase (PKMT) that methylates histone H3, the tumor suppressor p53 and the TBP-associated factor TAF10 (Nat Struct Mol Biol. 2006 Jan. 15; herein incorporated by reference in its entirety).

This assay quantifies the generation of the product S-adenosylhomocysteine (AdoHcy) using an enzyme-coupled assay with AdoHcy hydrolase (SAHH) from the archaeon *Sulfolobus solfataricus*. SAHH catalyzes the quantitative hydrolysis of AdoHcy to adenosine (Ado) and homocysteine (Hcy) in the presence of Ado deaminase, which converts Ado to inosine (FIG. 1). The concentration of the Hcy generated is subsequently determined through reaction with a sulfhydryl-sensitive fluorophore (e.g., ThioGlo 1), which fluoresces strongly upon conjugation of its maleimide moiety to a sulfhydryl group (Langmuir et al., Tetrahedron Lett. 36 (1995) 3989-3992). The coupled methyltransferase assay permits rapid and facile determination of HMT kinetics, avoids the handling and disposal of radioactive materials, and has been adapted for use with a fluorescence microplate reader for high-throughput analysis. In addition, this assay benefits from the SAHH-catalyzed hydrolysis of AdoHcy, which eliminates product inhibition of the methyltransferase and permits a more accurate determination of the steady state kinetic parameters. This assay is exemplified with the measurement of the kinetic parameters for the methylation of a histone H3 peptide by *Schizosaccharomyces pombe* CLR4, a histone H3 Lys-9-specific methyltransferase. The assay of the present invention finds use in a variety of research and clinical applications. Exemplary applications are described below.

I. HMT Assay

As described above, in some embodiments, the present invention provides a coupled fluorescent assay for the detection of histone methyltransferase activity (See e.g., FIG. 1). In some embodiments, the assay utilizes an AdoHcy hydrolase enzyme. The present invention is not limited to a particular AdoHcy hydrolase enzyme. In some exemplary embodiments, AdoHcy hydrolase from the archaeon *Sulfolobus solfataricus* is utilized. Preferred AdoHcy enzymes are those that lack Cys residues. Sulflhydryl groups of Cys residues can react with the detection moiety, thereby leading to a high fluorescence background (See e.g., Wang et al., BBRC 331: 351 [2005]). Preferred AdoHcy enzymes are also thermostable.

Additional AdoHcy hydrolases have been identified in other organisms and include, but are not limited to, AdoHcy from *Aspergillus fumigatus* (XM_747286), *Trypanosoma cruzi* (XM_810929), *Homo Sapiens* (NM_000687); *Prosopis juliflora* (DW359826); and *Mus musculus* (BK000547). Additional searches in UniProtKB/Swiss-Prot revealed the following matches: SAHH1_ARATH (O23255)—*Arabidopsis thaliana* (Mouse-ear cress); SAHH1_POPEU (P84533)—*Populus euphratica* (Euphrates poplar); SAHH2_ARATH (Q9LK36)—*Arabidopsis thaliana* (Mouse-ear cress); SAHH2_DROME (P50245)—*Drosophila melanogaster* (Fruit fly); SAHH2_HUMAN (O43865)—*Homo sapiens* (Human); SAHH2_POPEU (P84532)—*Populus euphratica* (Euphrates poplar); SAHH3_HUMAN (Q96HN2)—*Homo sapiens* (Human); SAHHA_XENLA (P51893)—*Xenopus laevis* (African clawed frog); SAHHB_XENLA (O93477)—*Xenopus laevis* (African clawed frog); SAHH_ACIAD (Q6FA43)—*Acinetobacter* sp. (strain ADP1); SAHH_AERPE (Q9YEF2)—*Aeropyrum pernix*; SAHH_AGRT5 (Q8UJ99)—*Agrobacterium tumefaciens* (strain C58/ATCC 33970); SAHH_ANASP (Q8YX05)—*Anabaena* sp. (strain PCC 7120); SAHH_ANOGA (O76757)—*Anopheles gambiae* (African malaria mosquito); SAHH_AQUAE (O67240)—*Aquifex aeolicus*; SAHH_ARCFU (O28279)—*Archaeoglobus fulgidus*; SAHH_BACFR (Q64MT2);—*Bacteroides fragilis*; SAHH_BACTN (Q8A407)-*Bacteroides thetaiotaomicron*; SAHH_BARHE (Q6G584)—*Bartonella henselae* (*Rochalimaea henselae*); SAHH_BARQU (Q6G1D6)—*Bartonella quintana* (*Rochalimaea quintana*); SAHH_BDEBA (Q6MNCO)—*Bdellovibrio bacteriovorus*; SAHH_BORBR (Q7WQX5)—*Bordetella bronchiseptica* (*Alcaligenes bronchisepticus*); SAHH_BORPA (Q7W1Z7)—*Bordetella parapertussis*; SAHH_BORPE (Q7VUL8)—*Bordetella pertussis*; SAHH_BRAJA (Q89HP6)—*Bradyrhizobium japonicum*; SAHH_BRUME (Q8YE49)—*Brucella melitensis*; SAHH_BRUSU (Q8FXZ7)—*Brucella suis*; SAHH_BURMA (Q62G22)—*Burkholderia mallei* (*Pseudomonas mallei*); SAHH_BURPS (Q63PT2)—*Burkholderia pseudomallei* (*Pseudomonas pseudomallei*); SAHH_CAEEL (P27604)—*Caenorhabditis elegans*; SAHH_CANAL (P83783)—*Candida albicans* (Yeast); SAHH_CATRO(P35007)—*Catharanthus roseus* (Rosy periwinkle) (Madagascar periwinkle); SAHH_CAUCR (Q9ABH0)—*Caulobacter crescentus*; SAHH_CHLTE (Q8KEG8)—*Chlorobium tepidum*; SAHH_CHRVO (Q7NZF7)—*Chromobacterium violaceum*; SAHH_CORDI (P61456)—*Corynebacterium diphtheriae*; SAHH_COREF (Q8FRJ4)—*Corynebacterium efficiens*; SAHH_CORGL (Q8NSC4)—*Corynebacterium glutamicum* (*Brevibacterium flavum*); SAHH_COXBU (Q83A77)—*Coxiella burnetii*; SAHH_DESVH (Q72EH1)—*Desulfovibrio vulgaris* (strain Hildenborough/ATCC 29579/NCIMB 8303); SAHH_DICDI (P10819)—*Dictyostelium discoideum* (Slime mold); SAHH_DROME (Q27580)—*Drosophila melanogaster* (Fruit fly); SAHH_GEOSL (P61617)—*Geobacter sulfurreducens*; SAHH_GLOVI (Q7NGI6)—*Gloeobacter violaceus*; SAHH_HALSA (Q9HN50)—*Halobacterium salinarium* (*Halobacterium halobium*); SAHH_HUMAN (P23526)—*Homo sapiens* (Human); SAHH_LEIDO (P36889)—*Leishmania donovani*; SAHH_LEPIC (Q75FU8)—*Leptospira interrogans* serogroup Icterohaemorrhagiae serovar copenhageni; SAHH_LEPIN (Q8EXV1)—*Leptospira interrogans*; SAHH LUPLU (Q9SP37)—*Lupinus luteus* (European yellow lupin); SAHH_LYCES (Q9SWF5)—*Lycopersicon esculentum* (Tomato); SAHH_MEDSA (P50246)—*Medicago sativa* (Alfalfa); SAHH_MESCR(P93253)—*Mesembryanthemum crystallinum* (Common ice plant); SAHH_METAC (Q8TRA5)—*Methanosarcina acetivorans*; SAHH_METCA (Q60CG8)—*Methylococcus capsulatus*; SAHH_METJA (Q58783)—*Methanococcus jannaschii*; SAHH_METKA (P58855)-*Methanopyrus kandleri*; SAHH_METMA (Q8PUQ4)—*Methanosarcina mazei* (*Methanosarcina frisia*); SAHH_METMP (Q6LYR8)—*Methanococcus maripaludis*; SAHH_METTH (O27673)—*Methanobacterium thermoautotrophicum*; SAHH_MOUSE (P50247)—*Mus musculus* (Mouse); SAHH_MYCBO (Q7TWW7)—*Mycobacterium bovis*; SAHH_MYCLE (Q9CCJ4)—*Mycobacterium leprae*; SAHH_MYCPA (Q73UK6)—*Mycobacterium paratuberculosis*; SAHH_MYCTU (P60176)—*Mycobacterium tuberculosis*; SAHH_NICSY (P68172)—*Nicotiana sylvestris*

(Wood tobacco); SAHH_NITEU (Q82WL1)—*Nitrosomonas europaea*; SAHH_NOCFA (Q5YQS7)—*Nocardia farcinica*; SAHH_PETCR (Q01781)—*Petroselinum crispum* (Parsley) (*Petroselinum hortense*); SAHH_PHASS (P50249)—*Phalaenopsis* sp; SAHH_PIG (Q710C4)—*Sus scrofa* (Pig); SAHH_PLACH (Q4XZZ5)—*Plasmodium chabaudi*; SAHH_PLAF7 (P50250)—*Plasmodium falciparum* (isolate 3D7); SAHH_PLAYO (Q7RKK8)—*Plasmodium yoelii yoelii*; SAHH_PNECA (Q12663)—*Pneumocystis carinii*; SAHH_PROMA (Q7V9P3)—*Prochlorococcus marinus*; SAHH_PROMM (Q7V926)—*Prochlorococcus marinus* (strain MIT 9313); SAHH_PROMP (Q7UZN3)—*Prochlorococcus marinus* subsp. *pastoris* (strain CCMP 1378/MED4); SAHH_PSEAE (Q9I685)—*Pseudomonas aeruginosa*; SAHH_PSESM (Q87V73)—*Pseudomonas syringae* pv. Tomato; SAHH_PYRAB (Q9UYK5)—*Pyrococcus abyssi*; SAHH_PYRAE (Q8ZTQ7)—*Pyrobaculum aerophilum*; SAHH_PYRFU (P50251)-*Pyrococcus furiosus*; SAHH_PYRHO (O58275)—*Pyrococcus horikoshii*; SAHH_PYRKO (Q5JED2)—*Pyrococcus kodakaraensis* (*Thermococcus kodakaraensis*); SAHH_RALSO (Q8Y387)—*Ralstonia solanacearum* (*Pseudomonas solanacearum*); SAHH_RAT (P10760)-*Rattus norvegicus* (Rat); SAHH_RHILO (Q98CM3)—*Rhizobium loti* (*Mesorhizobium loti*); SAHH_RHIME (Q92TC1)—*Rhizobium meliloti* (*Sinorhizobium meliloti*); SAHH_RHOBA (Q7TTZ5)—*Rhodopirellula baltica*; SAHH_RHOCA (P28183)—*Rhodobacter capsulatus* (*Rhodopseudomonas capsulata*); SAHH_RHOPA (Q6N2N5)—*Rhodopseudomonas palustris*; SAHH_RHOSH (O50562)—*Rhodobacter sphaeroides* (*Rhodopseudomonas sphaeroides*); SAHH_ROSDE (Q9ZNA5)—*Roseobacter denitrificans* (*Erythrobacter* sp. (strain OCh 114)); SAHH_SCHPO (O13639)—*Schizosaccharomyces pombe* (Fission yeast); SAHH_STRAA (Q936D6)—*Streptomyces argillaceus*; SAHH_STRAW (Q82DC9)—*Streptomyces avermitilis*; SAHH_STRAZ (Q8GGL7)—*Streptomyces atroolivaceus*; SAHH_STRCO (Q9KZM1)—*Streptomyces coelicolor*; SAHH_STRFR (P26799)—*Streptomyces fradiae*

SAHH_SULAC (Q4JAZ7);—*Sulfolobus acidocaldarius*; SAHH_SULSO(P50252)—*Sulfolobus solfataricus*; SAHH_SULTO (Q975T0)—*Sulfolobus tokodaii*; SAHH_SYNEL (Q8DGC8)—*Synechococcus elongatus* (*Thermosynechococcus elongatus*); SAHH_SYNPX (Q7U9Y3)—*Synechococcus* sp. (strain WH8102); SAHH_SYNY3 (P74008)—*Synechocystis* sp. (strain PCC 6803); SAHH_THEAC (Q9HKX4)—*Thermoplasma acidophilum*; SAHH_THEMA (O51933)—*Thermotoga maritime*; SAHH_THEVO (Q979Z4)—*Thermoplasma volcanium*; SAHH_TOBAC (P68173)—*Nicotiana tabacum* (Common tobacco); SAHH_TRIVA (P51540)—*Trichomonas vaginalis*; SAHH_WHEAT (P32112)—*Triticum aestivum* (Wheat); SAHH_XANAC (Q8PP84)—*Xanthomonas axonopodis* pv. *Citri*; SAHH_XANCP (Q8PCH5)—*Xanthomonas campestris* pv. *Campestris*; SAHH_XYLFA (Q9PEJ1)—*Xylella fastidiosa*; SAHH_XYLFT (Q87EI8)—*Xylella fastidiosa* (strain Temecula1/ATCC 700964); SAHH_YEAST (P39954)—*Saccharomyces cerevisiae* (Baker's yeast). Additional searches in UniProtKB/TrEMBL revealed the following matches: Q3BXC6_XANC5—*Xanthomonas campestris* pv. *vesicatoria* (strain 85-10); Q4H1G1_BETVU—*Beta vulgaris* (Sugar beet); Q4JTP5_CORJK—*Corynebacterium jeikeium* (strain $K_{411}$); Q5GW69_XANOR—*Xanthomonas oryzae* pv. *Oryzae*; Q5L7L6_BACFN—*Bacteroides fragilis* (strain ATCC 25285/NCTC 9343); Q5WV19_LEGPL—*Legionella pneumophila* (strain Lens); Q5X3N1_LEGPA—*Legionella pneumophila* (strain Paris); Q6DKD5_XENLA—*Xenopus laevis* (African clawed frog); Q6T2C8_PICPA—*Pichia pastoris* (Yeast); Q6YBX8_CRYPV—*Cryptosporidium parvum*; Q7YUF0_TRYCR—*Trypanosoma cruzi*; Q93CC0_MYCPA—*Mycobacterium paratuberculosis*. One skilled in the art recognizes that additional AdoHcy hydrolases may be identified based on their homology to known enzymes.

In some embodiments, the assay detects the product of the AdoHcy hydrolase reaction (Hyc-SH) by reaction with a reporter molecule. The present invention is not limited to a particular type of reporter molecule (e.g., phosphorescent reporter molecules, fluorescent reporter molecules (e.g., thiol sensitive fluorophores), chemoluminescent reporter molecules, colloidal metal reporting molecules, bioluminescent reporter molecules, radioisotope reporter molecules, phosphorescent reporter molecules, and colorimetric reporter molecules). Those of ordinary skill in the art will know of other suitable reporter molecules useful in the present invention.

In some embodiments, the reporter molecule is a fluorescent reporter molecule. In some exemplary embodiments, the fluorescent reporter molecule is ThioGlo 1 (available commercially from Calbiochem, San Diego, Calif.) is utilized. Preferred fluorescent or other reporter molecules react quickly with Hcy (e.g., within less than a minute and preferably within less than 10 seconds). Fast reaction times result in greater ease in quantitating the assay and determining the kinetics of methyltransferases. One skilled in the art recognizes that additional reagents and enzymes may be utilized in the assay of the present invention. For example, other sulfhydryl-sensitive fluorescence reporters include, but are not limited to, ThioGlo 3, ThioGlo5, and CPM {7-diethylamino-3-(4'-maleimidylphenyl)-4-methylcoumarin}. Suitable sulfhydryl-sensitive chromophoric reporters include, but are not limited to, DTNB {5,5'-dithiobis-(2-nitrobenzoic acid; can be used in a standard spectrophotometric or UV-Visble light assay}.

In some embodiments, the assay further includes adenosine deaminase, which deaminates adenosine to form inosine and ammonia. The deaminase is included in the coupled reaction to remove the adenosine generated from the SAHH-catalyzed hydrolysis of AdoHcy because the hydrolase can also catalyze the reverse reaction by condensing adenosine and Hcy to reform AdoHcy. This reverse reaction is not preferred because it reduces the Hcy concentration by regenerating AdoHcy, thereby leading to inaccuracies in determining the rates of methyltransfer. Thus, the inclusion of adenosine deaminase in the coupled reaction insures that the hydrolysis of AdoHcy by SAHH is driven to completion.

In some embodiments, the present invention provides kits for use in the measurement of HMT activity. In preferred embodiments, the kits comprise all of the components necessary for performing the HMT activity assay, including, but not limited to, enzymes, buffers, controls (e.g., Coenzyme-A (CoA-SH) for use in generating standard curves), and a reporter molecule (e.g., a phosphorescent reporter molecule, a fluorescent reporter molecule (e.g., a thiol sensitive fluorophore), a chemoluminescent reporter molecule, a colloidal metal reporting molecule, a bioluminescent reporter molecule, a radioisotope reporter molecule, a phosphorescent reporter molecule, and a colorimetric reporter molecule). In some embodiments, the kits contain all of the components necessary and/or sufficient for high-throughput screening assays (e.g., for use by a pharmaceutical company). In other embodiments, the kits are designed for use in a research setting (e.g., an academic research lab).

II. Drug Screening Methods

In some embodiments, the present invention provides methods of identifying potential ligands and drug targets of histone methyl transferases (HMTs). For example, in some embodiments, the present invention provides drug-screening methods utilizing the HMT assay described above. The drug screening methods of the present invention find use in the identification of modulators (e.g., enhancers or inhibitors) of HMT enzymes. As described above, histone methylation is involved in the transcriptional regulation of genes. As such, modulators of HMT enzymes find use in the treatment of a variety of disease states. In preferred embodiments, drug screening is performed using high-throughput screening methods.

Other screening assays identify substrates of HMT enzymes or variant HMT enzymes. Such assays find use in research (e.g., understanding of structure function relationships) as well as drug screening and drug design applications.

Any suitable source of HMT enzyme or activity may be utilized in the drug screening method of the present invention. For example, in some embodiments, HMT activity from homogenates of cells transfected with various HMT enzymes is used. In preferred embodiments, purified HMT enzymes are used as enzyme sources.

In some embodiments, the methods of the present invention are used in high-throughput screening methods. The fluorescence-based assay of the present invention provides a multiplate format suitable for high-throughput screening of modulators of HMT activity. High-throughput formats include, but are not limited to, multi-well plates, capillary systems, beads, and flow cytometry. In some embodiments, libraries of synthetic compounds or tissue extracts are screened for their ability to increase or decrease HMT. In other embodiments, HMT activity is stimulated by known activators and used to screen the compound libraries for inhibitors.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678-85 [1994]); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam, Anticancer Drug Des. 12:145 [1997]).

Examples of methods for the synthesis of molecular libraries can be found in the art, for example in: DeWitt et al., Proc. Natl. Acad. Sci. U.S.A. 90:6909 [1993]; Erb et al., Proc. Nat. Acad. Sci. USA 91:11422 [1994]; Zuckermann et al., J. Med. Chem. 37:2678 [1994]; Cho et al., Science 261:1303 [1993]; Carrell et al., Angew. Chem. Int. Ed. Engl. 33, 2059 [1994]; Carell et al., Angew. Chem. Int. Ed. Engl. 33:2061 [1994]; and Gallop et al., J. Med. Chem. 37:1233 [1994].

Libraries of compounds may be presented in solution (e.g., Houghten, Biotechniques 13:412-421 [1992]), or on beads (Lam, Nature 354:82-84 [1991]), chips (Fodor, Nature 364: 555-556 [1993]), bacteria or spores (U.S. Pat. No. 5,223,409; herein incorporated by reference), plasmids (Cull et al., Proc. Nad. Acad. Sci. USA 89:18651869 [1992]) or on phage (Scott and Smith, Science 249:386-390 [1990]; Devlin, Science 249:404-406 [1990]; Cwirla et al., Proc. Natl. Acad. Sci. 87:6378-6382 [1990]; Felici, J. Mol. Biol. 222:301 [1991]).

III. Pharmaceutical Compositions

The present invention further provides pharmaceutical compositions that may comprise modulators of HMT activity, alone or in combination with at least one other agent, such as a stabilizing compound, and may be administered in any sterile, biocompatible pharmaceutical carrier, including, but not limited to, saline, buffered saline, dextrose, and water.

The formulations of this invention are useful for parenteral administration, such as intravenous, subcutaneous, intramuscular, and intraperitoneal. Therapeutic administration of a polypeptide intracellularly can also be accomplished using gene therapy as described above.

As is well known in the medical arts, dosages for any one patient depends upon many factors, including the patient's size, body surface area, age, the particular compound to be administered, sex, time and route of administration, general health, and interaction with other drugs being concurrently administered.

Accordingly, in some embodiments of the present invention, drugs can be administered to a patient alone, or in combination with drugs or hormones or in pharmaceutical compositions where they are mixed with excipient(s) or other pharmaceutically acceptable carriers. In one embodiment of the present invention, the pharmaceutically acceptable carrier is pharmaceutically inert. In another embodiment of the present invention, drugs may be administered alone to individuals subject to or suffering from a disease.

Depending on the condition being treated, these pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration.

For injection, the pharmaceutical compositions of the invention may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art.

In other embodiments, the pharmaceutical compositions of the present invention can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated.

Pharmaceutical compositions suitable for use in the present invention include compositions wherein the active ingredients are contained in an effective amount to achieve the intended purpose. For example, an effective amount of may be that amount that suppresses a disease state associated with abnormal HMT activity. Determination of effective amounts is well within the capability of those skilled in the art, especially in light of the disclosure provided herein.

In addition to the active ingredients these pharmaceutical compositions may contain suitable pharmaceutically acceptable carriers comprising excipients and auxiliaries that facilitate processing of the active compounds into preparations that can be used pharmaceutically. The preparations formulated for oral administration may be in the form of tablets, dragees, capsules, or solutions.

The pharmaceutical compositions of the present invention may be manufactured in a manner that is itself known (e.g., by means of conventional mixing, dissolving, granulating, dragee-making, levigating, emulsifying, encapsulating, entrapping or lyophilizing processes).

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethyl-cellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compounds, (i.e., dosage).

Pharmaceutical preparations that can be used orally include push-fit capsules made of gelatin, as well as soft, sealed capsules made of gelatin and a coating such as glycerol or sorbitol. The push-fit capsules can contain the active ingredients mixed with fillers or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Compositions comprising a compound of the invention formulated in a pharmaceutical acceptable carrier may be prepared, placed in an appropriate container, and labeled for treatment of an indicated condition.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5 that is combined with buffer prior to use.

For any compound used in the method of the invention, the therapeutically effective dose can be estimated initially from cell culture assays. Then, preferably, dosage can be formulated in animal models (particularly murine models) to achieve a desirable circulating concentration range.

A therapeutically effective dose refers to that amount of peptide that ameliorates symptoms of the disease state. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state; age, weight, and gender of the patient; diet, time and frequency of administration, drug combination(s), reaction sensitivities, and tolerance/response to therapy. Long acting pharmaceutical compositions might be administered every 1 to 4 days, every week, or once every two weeks depending on half-life and clearance rate of the particular formulation. Standard (non-long acting) formulations may be administered every day or several (e.g., 2-4) times a day.

Normal dosage amounts may vary from 0.1 to 100,000 micrograms, up to a total dose of about 1 g, depending upon the route of administration. Guidance as to particular dosages and methods of delivery is provided in the literature (See e.g., U.S. Pat. Nos. 4,657,760; 5,206,344; or 5,225,212, all of which are herein incorporated by reference). Administration to the bone marrow may necessitate delivery in a manner different from intravenous injections.

EXPERIMENTAL

The following examples serve to illustrate certain preferred embodiments and aspects of the present invention and are not to be construed as limiting the scope thereof.

EXAMPLE 1

Development of Histone Methyltransferase Assay

This Example describes the development of a coupled fluorescent assay for detection of histone methyltransferase activity.

A. Materials and Methods

Reagents

Bovine type X adenosine deaminase, the sodium salt of coenzyme A (CoA), S-adenosyl-L-methionine, and oxidized β-nicotinamide adenine dinucleotide (NAD+) were purchased from Sigma. AdoMet was further purified by ion exchange to remove impurities present in the commercially available cofactor, as detailed by Barker and co-workers (Chirpich et al., J. Biol. Chem. 245 (1970) 1778-1789). Thio-Glo 1 [10-(2,5-dihydro-2,5-dioxo-1H-pyrrol-1-yl)-9-methoxy-3-oxo-, methyl ester 3H-naphthol(2,1-β)pyran-S-carboxylic acid] and Fraction V bovine serum albumin (BSA) were obtained from Calbiochem and Fisher, respectively. Free cysteines in BSA were covalently blocked with N-ethylmaleimide to reduce the sulfhydryl background in the assay, as previously described (Trievel et al., Anal. Biochem. 287 (2000) 319-328). A synthetic peptide comprising the first 15 residues of histone H3 (sequence: ARTKQTARKSTG-GKA (SEQ ID NO:1), where K is the methylation site of CLR4) was obtained from American Peptide, (Sunnyvale, Calif.) and supplied as 2.0-mg lyophilized aliquots. Peptide samples were dissolved in Milli-Q water to the appropriate concentration prior to use in HMT assays.

SsSAHH Cloning and Purification

Figure 2:
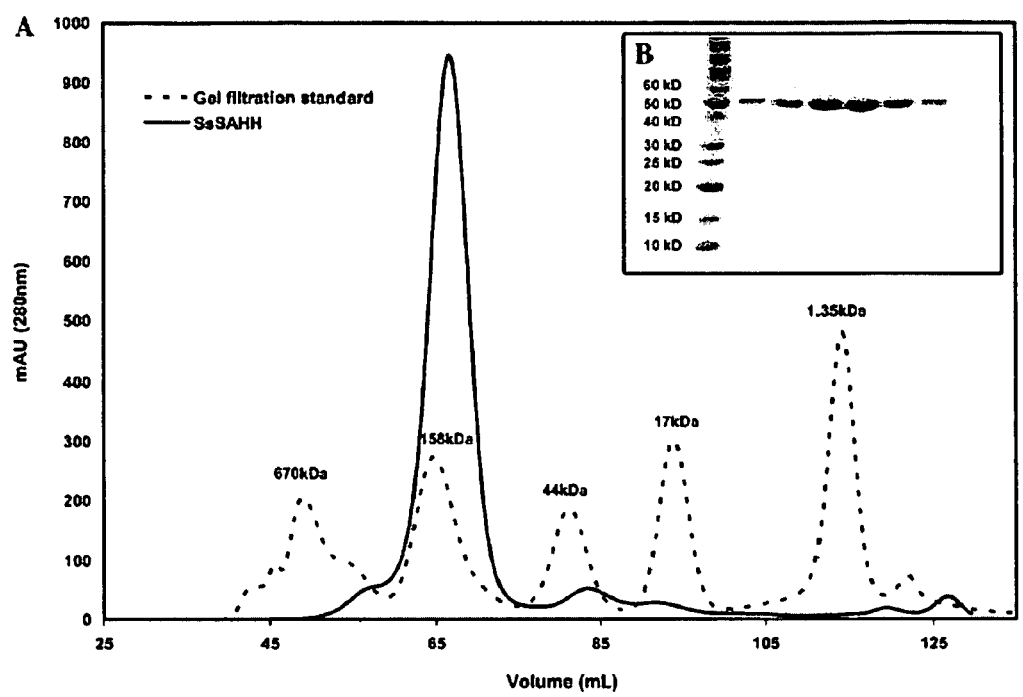
FIG. 2 shows purification of recombinant *S. solfataricus* SAHH (SsSAHH). (A) Superdex 200 gel filtration of SsSAHH. (B) SDS-PAGE electrophoresis of the peak fractions from the Superdex 200 purification of SsSAHH.

The DNA encoding SAHH from *S. solfataricus* (SsSAHH) was amplified from genomic DNA (ATCC) and cloned into the pHIS2 parallel expression vector using BamH1 and EcoR1 restriction enzyme sites (Sheffield et al., Protein Expr. Purif. 15 (1999) 34-39). The pHIS2 vector has an N-terminal hexahistidine tag and a tobacco etch virus (TEV) protease cleavage site to facilitate metal affinity purification and removal of the tag, respectively. SsSAHH was overexpressed in BL21 Codon Plus RIL cells (Stratagene) at 37° C. for 3 h with 0.1 mM isopropyl β-D-thiogalactoside. Harvested cells were lysed in 50 mM sodium phosphate, pH 7.0, 500 mM NaCl, and 10% glycerol buffer using a combination of lysozyme (5 mg), flash freeze-thaw cycles, and sonication, followed by centrifugation at 16,000 rpm at 4° C. The soluble enzyme was then loaded onto a Talon (Clontech) $Co^{2+}$ immobilized metal affinity column preequilibrated with lysis buffer and eluted with a linear gradient of 0-500 mM imidazole. The peak fractions containing SsSAHH were then pooled, concentrated, and digested with the TEV S219V mutant (Kapust et al., Protein Eng. 14 (2001) 993-1000) during dialysis against 50 mM Tris, pH 8.0, 150 mM NaCl, 1 mM EDTA, and 1 mM dithiothreitol buffer at room temperature for 16 h. The digested protein was then purified by elution over a second Talon column to remove any uncleaved enzyme, the His-tagged TEV protease, and other contaminants. The partially purified SsSAHH was subsequently ammonium-sulfate-precipitated to produce the apoprotein and reconstituted with NAD+ to obtain the fully active enzyme as described by Borchardt and co-workers (Yuan et al., J. Biol. Chem. 268 (1993), 17030-17037). Finally, SsSAHH was concentrated and loaded onto a Superdex 200 (Amersham Biosciences) gel filtration column and purified isocratically in 20 mM potassium phosphate, pH 7.2, 100 mM NaCl, and 1 mM EDTA buffer. SsSAHH eluted as a tetramer (FIG. 2A) as previously reported (Porcelli et al., Protein Expr. Purif. 18 (2000) 27-35) and was judged to be at least 99% pure by SDS-PAGE (FIG. 2B). Peak fractions from gel filtration were concentrated to approximately 60 mg/mL, as determined by the Bradford assay using BSA as a standard (Bradford, Anal. Biochem. 72 (1976) 248-254). Purified SsSAHH was either stored at room temperature in gel filtration buffer containing 0.01% sodium azide or flash-frozen in liquid nitrogen and stored at 80° C.

CLR4 Cloning and Purification

A fragment encoding residues 192-490 of CLR4 was amplified from the S. pombe genomic clone SPBC428.08c (Sanger Institute, Cambridge, UK) and ligated into pHIS2 using BamHI and EcoRI restriction sites. CLR4 was overexpressed at 15° C. in BL21 Codon Plus RIL cells and purified to homogeneity as described for pea Rubisco large subunit methyltransferase (pLSMT) (Trievel et al., Cell 111 (2002) 91-103).

HMT Assays

All methyltransferase assays were performed at 37° C. in a cocktail of 100 mM Hepes, pH 7.5, and 0.01% BSA. Before conducting the kinetic analysis of CLR4, a series of control experiments were conducted to establish the optimum concentrations of SsSAHH and Ado deaminase for the coupled reaction. The linearity of the assay with respect to the enzyme concentration was determined by varying the concentration of CLR4 and measuring initial velocities while fixing both substrate concentrations. After completing the control experiments, kinetic parameters for the methylation of the histone H3 peptide by CLR4 were measured. Assay cocktails were prepared with 5 µM SsSAHH, one unit of Ado deaminase (defined as deaminating 1.0 µM of Ado per minute), and 1 µM CLR4 in 1.5-mL microfuge tubes. The peptide concentration was varied above and below the $K_M$ value to provide accurate measurements of the Michael is constant and turnover number. Assays were initiated by the addition of a saturating concentration of AdoMet (50 µM) in a final assay volume of 310 µL. Aliquots (50 µL) were taken at evenly spaced time intervals starting at time zero and quenched with 50 µL of cold isopropanol in individual wells of a black 96-well polypropylene plate (Corning) that was incubated on ice. The cold isopropanol quench is necessary to inactivate SsSAHH, which retains partial enzymatic activity in 50% alcohol solutions at ambient temperatures (Porcelli et al., Biochim. Biophys. Acta 1164 (1993) 179-188). After completing the assay, 100 µL of 20 µM ThioGlo 1 solution in dimethyl sulfoxide was added to each well and allowed to react for 10 min in the dark at room temperature. Fluorescence was then measured in a Tecan Genios Pro fluorescence microplate reader using 400 nm excitation and 515 nm emission filters with a gain setting of 27. To determine the quantity of Hcy generated in the assay, standard curves were measured in duplicate each day with reduced CoA, whose concentration was independently determined by its absorbance at 260 nm ($\epsilon_{260\,nm}$=15,400 $M^{-1}$ $cm^{-1}$). Assay cocktails (50 µL) were prepared with 0-10 µM CoA (0-500 pmol) in 2 µM increments and mixed with isopropanol (50 µL) and ThioGlo 1 solution (100 µL). Fluorescence was then measured as previously described and exhibited a linear relationship with the CoA concentration.

Data Analysis

HMT assays with CLR4 were performed in triplicate for each substrate concentration. After converting the fluorescence values to Hcy concentration using the conversion factor calculated from the CoA calibration curves, initial velocities ($v_o$) were determined by plotting the Hcy concentration versus time and calculating the least squares linear fit to the data with Excel (Microsoft). The values of $v_o$ were then plotted versus substrate concentration ([S]) and fit to a hyperbolic function for the Michaelis-Menten equation (Eq. (1)) in SigmaPlot (Systat Software) to derive the kcat and $K_M$ values.
$v_0 = k_{cat}[E_T][S]/([S]+K_M)$.

B. Results

Selection of *S. solfataricus* S-Adenosylhomocysteine Hydrolase

The fluorescent HMT assay couples the generation of the methyltransferase product AdoHcy to its hydrolysis to Hcy and Ado via SAHH (FIG. 1). The Hcy concentration can be subsequently determined using a sulfhydryl sensitive chromophore or fluorophore, depending on the level of sensitivity required. SAHH is a highly conserved enzyme found throughout all kingdoms of life and catalyzes the reversible hydrolysis of AdoHcy to maintain intracellular AdoHcy:Hcy homeostasis (Kloor et al., Trends Pharmacol. Sci. 25 (2004) 294-297). To identify an appropriate SAHH for the coupled assay, an extensive search of the ExPASy Protein Database was conducted for homologs of this enzyme from various species. An ortholog from the archaeon S. solfataricus (SsSAHH) was selected and subsequently cloned, expressed, and purified to homogeneity (FIGS. 2A and B). SsSAHH possesses several properties that are advantageous for the coupled methyltransferase assay. First, SsSAHH completely lacks cysteine residues, permitting it to be used at high concentrations in the assay cocktail without generating fluorescence background that would interfere with quantification of the Hcy concentration. Second, the properties of this enzyme have been previously characterized, and it has been shown to be relatively thermostable and resistant to numerous denaturants including 6 M guanidine hydrochloride, 0.075% SDS, and 50% solutions of various alcohols (Porcelli et al., Biochim. Biophys. Acta 1164 (1993) 179-188). Third, the expression and purification of the recombinant His-tagged protein is straightforward and yields a significant quantity of homogeneous enzyme (approximately 20 mg/L of culture) (FIG. 2A). Taken together, the chemical and physical properties of SsSAHH are well suited for the fluorescent methyltransferase assay.

Development of the Coupled Fluorescent HMT Assay

The method for detecting the Hcy generated by the coupled reaction with SsSAHH was adapted from a fluorescent HAT assay that quantifies the release of CoA using the sulfhydryl-sensitive fluorophore, 7-diethylamino-3-(40-maleimidylphenyl)-4-methylcoumarin (CPM) (Trievel et al., Anal. Biochem. 287 (2000) 319-328). Several modifications of this technique have been implemented to increase its sensitivity for quantifying the concentration of Hcy generated in the HMT assay. CPM was replaced with ThioGlo 1, a naphthopyranone-based fluorophore that fluoresces strongly at 513 nm upon reaction of its maleimide moiety with a sulfhydryl group. This dye is utilized in many applications that require sulfhydryl labeling, including the quantification of the small molecular thiols (Wright et al., Anal. Biochem. 265 (1998) 8-14), thereby making it an appropriate choice to measure the Hcy generated in the coupled reaction. Moreover, ThioGlo 1 has several advantages over CPM including a fivefold higher quantum yield of its sulfhydryl adduct ($\Phi_{513\,nm}$=0.65 versus $\Phi_{475\,nm}$=0.13 for CPM), a larger Stokes shift, and greater resistance of its maleimide moiety to hydrolysis under aqueous conditions). To compare the sulfhydryl detection limits of the two fluorophores, a series of standard curves were performed with varying concentrations of CoA as described under Materials and methods. Using ThioGlo 1, it was possible to detect CoA quantities between 100 and 500 pmol in black microplates, which is comparable to the results obtained using CPM with white microplates (Trievel et al., 2000, supra). However, black microplates exhibit less fluorescence background than their white counterparts (Ayers et al., Anal. Biochem. 154 (1986) 186-193), resulting in a gain in the signal-to-noise ratio in the HMT assay versus the previously reported CPM/white microplate combination (Trievel et al., 2000, supra).

Once the calibration analysis with ThioGlo 1 and CoA were completed, a series of controls were conducted to optimize the conditions for the fluorescent HMT assay. Initial velocities were determined discontinuously by quenching aliquots of the assay at discrete intervals and then reacting the samples with ThioGlo 1 solution. After measuring the fluorescence, the resulting kinetic data were fit with a linear regression function to determine the enzymatic rate. This protocol was adopted in favor of measuring the velocities continuously with ThioGlo 1, which could result in modification of cysteines in the HMT and a loss in enzymatic activity, as previously discussed for the fluorescent HAT assay (Trievel et al., 2000, supra).

After establishing the linearity of the initial velocities in the HMT assay, the rates were optimized by altering the concentrations of the two coupling enzymes, SsSAHH and Ado deaminase. The inclusion of the deaminase in the coupled reaction eliminates the SsSAHH-catalyzed condensation of Ado and Hcy, which regenerates Ado-Hcy (FIG. 1). One unit of Ado deaminase and an SsSAHH concentration fivefold higher than the HMT concentration yielded optimal initial velocities; thus, the coupling enzymes were not rate limiting in the assay. Higher concentrations of each enzyme were also tested and had no apparent effect on the overall rates. Utilizing this enzyme coupled system, it was possible to run fluorescent HMT assays for 30 min with no detectable decrease in the methyltransfer rate over time. Conversely, product inhibition of G9A, a histone H3 Lys-9/27 methyltransferase (Tachibana et al., J. Biol. Chem. 276 (2001) 25309-25317), was observed within approximately 5 min of initiating the radiometric assay (Patnaik et al., J. Biol. Chem. (2004)). Thus, the SsSAHH/Ado-deaminase-coupled reaction not only provides a convenient fluorescent "handle" for assaying methyltransferases but also benefits from abolishing product inhibition by AdoHcy.

Figure 3:
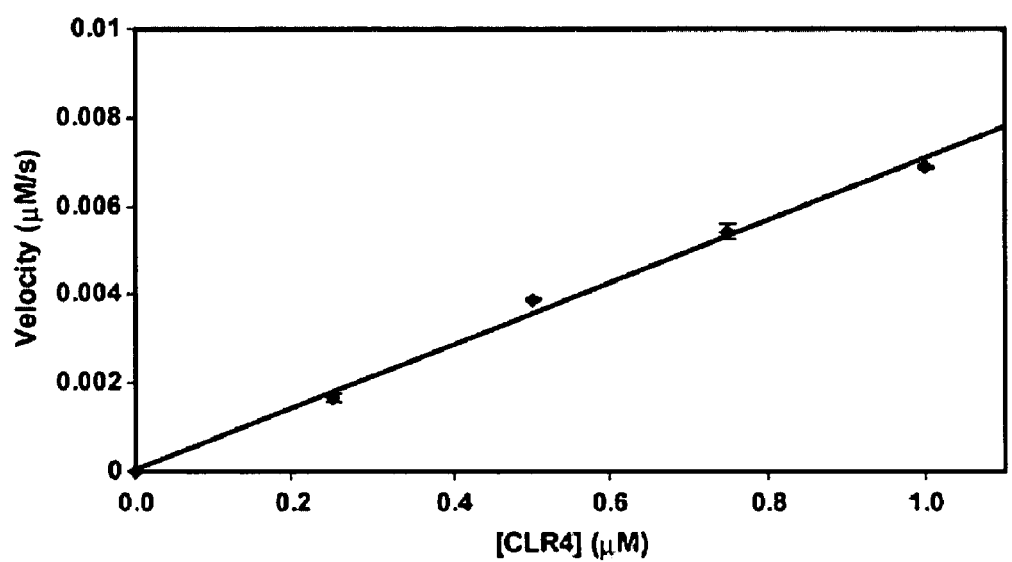
FIG. 3 shows the linear relationship between CLR4 concentration and initial velocity.

A final set of controls was performed to confirm that the coupled fluorescent assay is linear with respect to initial velocity and enzyme concentration. The rates of methylation of the histone H3 peptide were measured as function of the concentration of CLR4. As illustrated in FIG. 3, the initial velocities are linear with CLR4 concentrations from zero to 1.0 μM. This plot also reveals that, in the absence of CLR4, the nonenzymatic rate of histone methylation by AdoMet is negligible at pH 7.5.

Kinetic Analysis of CLR4

Figure 4:
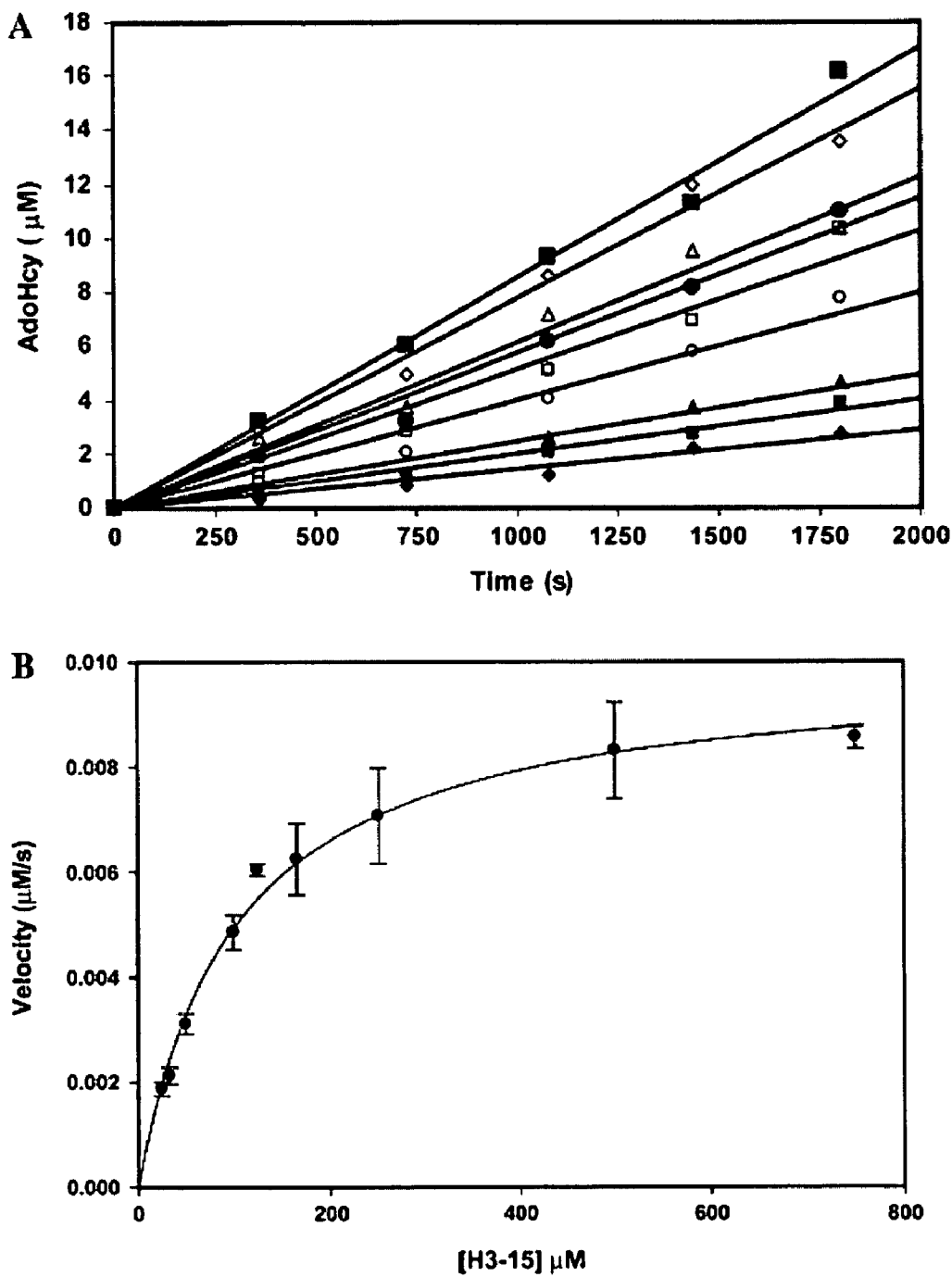
FIG. 4 shows measurement of the kinetic parameters of S. pombe CLR4. (A) HMT assays were carried out in triplicate with histone H3 peptide (H3-15) concentrations of 25 µM (♦), 33 µM (■), 50 µM (▲), 100 µM (○), 125 µM (□), 166 µM (●), 250 µM (Δ), 500 µM (◊), and 750 µM (■). (B) Michaelis-Menten plot of initial velocity versus substrate concentration.

After completing the control experiments for the fluorescent HMT assay, the steady state kinetic properties of CLR4 were analyzed. Although this HMT has a well-established connection to transcriptional silencing in S. pombe, its kinetic parameters have not been determined. Using the fluorescent assay, the kcat (0.0099±0.0003 s$^{-1}$) and $K_M$ (101±9 μM) values for the methylation of the histone H3 peptide by CLR4 were assayed (FIGS. 4A and B).

The turnover number correlates well with other HMTs whose kinetics have been characterized with the radiometric assay, including human SET7/9 (0.004 s$^{-1}$) (Trievel et al., Cell 111 (2002) 91-103), mouse G9A (0.024 s$^{-1}$) (Patnaik et al., supra), Drosophila SU(VAR)3-9 (0.11 s$^{-1}$) [11], and pLSMT (0.0383 s$^{-1}$), a plant homolog of HKMTs (Trievel et al., 2002, supra). The Michaelis constant for CLR4 is higher than those published for the other enzymes. The present invention is not limited to a particular mechanism. Indeed, an understanding of the mechanism is not necessary to practice the present invention. Nonetheless, it is contemplated that the differences in the $K_M$ values may simply reflect weaker binding of histone H3 to CLR4 in comparison with the other methyltransferases and their cognate substrates. Alternatively, the variations in the Michaelis constants may arise from differences in the substrates and conditions that were employed in the other methyltransferase assays. For example, the kinetic values of G9A were determined with a peptide of the N-terminal 19 residues of histone H3, whereas SET7/9 and LSMT were assayed with calf thymus histone H3 and spinach Rubisco, respectively. These substrates are larger than the 15-residue histone H3 peptide used to assay CLR4 and may bind with higher affinity to their respective HMTs, accounting for the differences in the Km values. In addition, many of the other assays were run at pH values above 8.0, a range in which these enzymes exhibit their maximal activity. In contrast, the fluorescent assays described herein were performed at pH 7.5, which more closely mimics physiological conditions in the nucleus.

The coupled fluorescent assay presented here serves as a general tool for studying HMTs. The adaptation of this assay for use with a fluorescent microplate reader is a significant advantage over the currently employed radiometric assay and facilitates high-throughput analysis of the kinetic properties of these enzymes. Given the multitude of HMTs that have been recently identified, quantitative analysis of the substrate specificities of these enzymes is useful to revealing their functions in transcriptional regulation and DNA damage checkpoint control. Moreover, several HMTs have recently been implicated in cancer (Schneider et al., Trends Biochem. Sci. 27 (2002) 396-402), a high-throughput assay accelerates the development and screening of inhibitors directed against these enzymes. This assay is applicable to virtually all AdoMet-dependent methyltransferases and provides a universal method for characterizing the kinetic properties of this diverse and important family of enzymes.

EXAMPLE 2

Further Characterization of hSET8

This Example describes the use of the methyltransferase assay of the present invention to further characterize hSET8.

A. Materials and Methods

Cloning and Expression of hSET8

A construct of hSET8 encoding residues 191-352 was cloned into the parallel expression vector pHIS2 using BamHI and XhoI restriction sites (Sheffield et al., Protein Expr. Purif. 15: 34-39, 1999). The enzyme was then overexpressed in *Escherichia coli* BL21 (DE3) Codon Plus RIL cells Stratagene) at 17° C. and purified to homogeneity using Talon Co2+ (Clontech) affinity and Superdex 75 (Amersham Biosciences) gel filtration chromatographies, essentially as reported for pea Rubisco LSMT (Trievel et al., Cell 111: 91-103, 2002) (with the exception that gel filtration was performed in 20 mM Tris-HCl at pH 7.0, 100 mM NaCl, and 10 mM β-mercaptoethanol). Mutants of hSET8 were prepared using the QuikChange Site-Directed Mutagenesis Kit (Stratagene), and the sequences were verified by dideoxy sequencing. Mutants of hSET8 were expressed and purified as described for the wild-type enzyme.

Histone H4 Peptides

Wild-type and mutant histone H4 peptides (sequence: A15-K16-R17-H18-R19-K20-V21-L22-R23-D24) were purchased from New England Peptide, Inc. Peptides were synthesized with N-terminal acetyl and C-terminal amide groups and were delivered as 2.5-mg lyophilized aliquots that were resuspended in deionized water to the appropriate concentration prior to use.

Crystallization and Structure Determination

Selenomethionyl-derivatized hSET8 containing an I220M mutation was prepared according to the protocol of Doublie (1997). Native and SeMet crystals of the ternary complex were obtained in 25%-35% Pentaerythritol Ethoxylate (15/4), 50 mM $(NH_4)_2SO_4$, and 100 mM Bis-TRIS (pH 6.0-7.0) at 4° C. using 40 mg/mL hSET8 and a twofold molar ratio of the histone H4 peptide and AdoHcy. Crystals were then harvested in mother liquor and directly flash-frozen in liquid nitrogen. A selenomethionyl multiwavelength anomalous dispersion (MAD) experiment was conducted at the 32-ID beamline of COM-CAT at the Advanced Photon Source Synchrotron. Data were collected on a single crystal of the I220M mutant at the selenium edge with a Mar165 CCD detector (Mar Research) and subsequently processed and scaled using Denzo and Scalepack (Otwinowski and Minor, Methods Enzymol. 276: 307-326, 1997). A complete high-resolution data set was also collected to 1.45 Å using a single crystal of native hSET8. After processing and scaling the peak, inflection point, and high remote wavelength data sets, the data were submitted for structure determination in the Automated Crystallographic System (Aces) (Brunzelle et al., Acta Crystallogr. D Biol. Crystallogr. 59: 1138-1144, 2003). The best solution resulted from the HySS (Grosse-Kunstleve and Adams, Acta Crystallogr. D Biol. Crystallogr. 59: 1966-1973, 2003), SHARP (de la Fortelle and Bricogne, Methods Enzymol. 276: 474-492, 1997), DM/Solomon (Cowtan and Main 1993; Abrahams and Leslie 1996), and ARP/wARP (Perrakis et al., Nat. Struct. Biol. 6: 458-463, 1999) pathway. The 2.0 Å experimental map was readily interpretable and permitted automated model building in ARP/wARP. The resulting hSET8 model was then used for molecular replacement with the native data set in MOLREP (Vagin and Teplyakov, J. Appl. Cryst. 30: 1022-1025, 1997). Four molecules were located in the triclinic cell, which were then used for model building in O (Jones et al., Acta Crystallogr. A 47: 110-119, 1991) and refinement in REFMAC (Murshudov et al., Acta Cryst. D 53: 240-255, 1997). In later stages of refinement, water molecules were added, and residues with alternative conformations were modeled. In the final model, Ala-15 and the side chain of Lys-16 were omitted due to poor electron density in the N terminus of the H4 peptide. The final structure has Rworking and Rfree values of 16.9% and 19.9%, respectively and excellent geometry with none of the nonglycine residues present in the disallowed regions of the Ramachandran plot. Structural figures were generated and rendered in PyMOL.

Isothermal Titration Calorimetry

The equilibrium dissociation constants of wild type and mutants of hSET8 and histone H4 were determined using a VP-ITC calorimeter (MicroCal, LLC). The enthalpies of binding of wild type and mutants of hSET8 (60-120 μM) and the histone H4 peptide (1.0-2.0 mM) were measured at 20° C. in 20 mM sodium phosphate (pH 7.0) and 100 mM NaCl. A saturating concentration of AdoHcy (1.0-2.0 mM) was used in all titrations. ITC data were subsequently analyzed using Origin 7.0 (OriginLab Corp.) with blank injections of ligand into buffer subtracted from the experimental titrations prior to data analysis. All of the calculated binding curves had N-values between 0.85 and 1.00.

Histone Methyltransferase Assays

The steady-state kinetic parameters for wild type and mutants of hSET8 and histone H4 were determined using a coupled fluorescent methyltransferase assay laboratory. S-adenosylmethionine (AdoMet) was purified by cation exchange to remove impurities present in the commercially available cofactor, as described by Barker and coworkers (Chirpich et al., J. Biol. Chem. 245: 1778-1789, 1970). Assays were performed in 100 mM HEPES buffer (pH 7.5) and 0.02% maleimide-treated BSA with 0.5-2.0 μM hSET8, a saturating concentration of AdoMet (50 μM), and varying concentrations of histone H4 peptide. Assays were performed in duplicate with a final volume of 150 µL. To determine the $K_M$ and kcat values, peptide concentrations were varied from 0.05 to 4.0 mM. In cases in which the $K_M$ value was too high to be accurately measured (>2.5 mM), the substrate specificity (kcat/$K_M$) was determined by varying the H4 peptide concentration (0.16-0.64 mM) below the $K_M$ value. This simplification permits the kcat/$K_M$ value to be determined from the linear relationship between the initial velocity and substrate concentration within this range of the Michaelis-Menten plot. Fluorescence was measured using a GeniosPro microplate reader (Tecan), and initial velocities were calculated by a linear fit from the plot of the fluorescence values versus time. The steady-state kinetics parameters were then calculated by plotting the velocity versus peptide concentration and fitting the Michaelis-Menten equation to the data in SigmaPlot (Systat Software, Inc.).

Mass Spectrometry Analysis

Histone methyltransferase assays were performed with wildtype hSET8 and the Tyr-245 and Tyr-334 mutants (5 µM) as described above and were quenched after 15 min or 24 h by the addition of 0.5% trifluoroacetic acid. Aliquots of the samples were cocrystallized with α-cyano-4-hydroxycinnamic acid (1:1), applied on the target, and dried at room temperature. The mass spectra were acquired on the TofSpec 2E MALDI-TOF mass spectrometer (Waters, Inc.) in reflectron mode, with each spectrum representing the average of 50 laser shots. Close external calibration was used based on the following mixture: bradikinin fragment 1-8, m/z=904.41 (for [M+H]+); angiotensin II, m/z=1046.54; [Glu1]-fibrinopeptide B, m/z=1570.68; ACTH (clip 18-39), m/z=2465.20.

B. Results and Discussion

Overall Structure of the hSET8 Ternary Complex

To elucidate the structure of hSET8 in complex with histone H4, a construct of the enzyme encoding the catalytic SET domain (residues 191-352) was co-crystallized with a 10-residue H4 peptide (A-K-R-H-R-K20-V-L-R-D) and the product AdoHcy. Removal of the N-terminal 190 residues was necessary in order to obtain diffraction quality crystals of the complex, but did not impair the activity of the enzyme. The structure was determined at 2.0 Å resolution by selenomethionyl multiple wavelength anomalous dispersion (MAD) phasing using an I220M mutant to enhance the Se anomalous signal. The experimentally phased structure was then used as a molecular replacement model to determine the structure of the wild-type hSET8 in complex with the histone H4 peptide and AdoHcy at 1.45 Å resolution.

The overall fold of the catalytic domain of hSET8 is structurally conserved with other SET-domain PKMTs (Trievel, Crit. Rev. Eukaryot. Gene Expr. 14: 147-170, 2004). The SET domain is composed of a single turn $3_{10}$ helix ($3_{10-1}$) and 12 β-strands (β 1-β 12) arranged into four antiparallel β-sheets and a single parallel β-sheet (Trievel et al., 2002, supra). An α-helix (α2) is inserted between the β5- and β6-strands of the SET domain, as is observed in the structures of the histone H3 methyltransferases *Neurospora* DIM-5 (Zhang et al., Mol. Cell. 12: 177-185, 2002) and human SET7/9 (Wilson et al., Cell 111: 105-115, 2002). This helix forms the inserted SET or iSET region, and variations in the sequence and structure of this motif play a key role in determining the substrate specificity of different PKMTs (Xiao et al., Curr. Pin. Struct. Biol. 13: 699-705, 2003b). In contrast, the N- and C-terminal regions that flank the SET domain of hSET8 (referred to as the onset and cSET regions, respectively) are not conserved in the structures of other histone methyltransferases. In the nSET region, a single α-helix (α1) precedes the SET domain, similar to the N-terminal α helix of Rubisco large subunit methyltransferase (LSMT), a plant SET-domain enzyme (Trievel et al., 2002, supra). The cSET region of hSET8 is composed of a short α-helix (α3) and a $3_{10}$ helix ($3_{10-2}$) that pack against the cofactor and protein substrate-binding sites. Mutations within this region abrogate substrate binding and catalysis (see below), agreeing with the truncation studies reported by Zhang and colleagues (Fang et al., Curr. Biol. 12: 1086-1099, 2002).

AdoMet-Binding Site

The product AdoHcy adopts a horseshoe-shaped conformation in the cofactor-binding pocket that is formed by the β1-β2 turn, the loop preceding β6, the β8-strand, and the α3-helix in the cSET region. The adenine moiety of AdoHcy is sandwiched between the indole ring of Trp-349 and the aliphatic side chain of Lys-226, and the purine N6 and N7 atoms hydrogen-bond to the backbone carbonyl and amide groups of His-299, respectively. At the opposite end of the cofactor, the positively charged α-amino group is recognized by a trigonal array of hydrogen bonds with the main chain carbonyl oxygens of Lys-226 and Arg-228 and the amide Oδ of Asn-298. In addition, the carboxylate moiety of the AdoHcy forms a highly conserved salt-bridge interaction with the guanidinium group of Arg-228 and also hydrogen-bonds to the hydroxyl of Tyr-271. Overall, the cofactor-binding mode is structurally conserved with other SET-domain methyltransferases and serves to orient the methyl group of AdoMet into the methyltransfer pore during catalysis (Trievel, 2004, supra).

Despite these similarities, a striking difference is observed in the interactions with the ribose moiety of AdoHcy in the hSET8 ternary complex. In the structures of other SET-domain PKMTs, the ribose hydroxyls of the cofactor are either solvent-exposed, such as in hSET7/9 (Xiao et al., Nature 421: 652-656, 2003a) and Rubisco LSMT (Trievel et al., 2002, supra), or hydrogen-bonded with neighboring residues, as is observed in DIM-5 (Zhang et al., Mol. Cell 12: 177-185, 2003). However in the hSET8 ternary complex, the 3'-OH hydroxyl engages in a direct hydrogen bond with the imidazole moiety of His-18 in the histone H4 peptide. This novel substrate-cofactor interaction does not occur within other SET-domain enzymes because the residues that line the floor of the protein substrate-binding cleft occlude the AdoMet-binding pocket, preventing direct contact between the histone and the cofactor. Using isothermal titration calorimetry (ITC), it was determined that mutation of His-18 to phenylalanine modestly affects the affinity of hSET8 for histone H4, whereas substitution of this residue by alanine (H18A) completely abolishes binding. Both the H18F and H18A substitutions severely abrogate AdoHcy binding, suggesting that the hydrogen bond between His-18 and the cofactor is important for high-affinity binding of AdoMet. However, steady-state kinetic analysis of native hSET8 and the His-18 mutants reveals that the H18F mutant exhibits only a slight reduction in its substrate specificity (kcat/KM value) in comparison to the native H4 peptide, while the H18A mutant completely eliminates histone H4 methylation by hSET8. Collectively, these results indicate that the hydrogen bond between the cofactor and His-18 in histone H4 enhances the affinity of AdoMet for hSET8, but is not essential for catalysis.

Histone H4 Recognition by hSET8

The experimental map obtained from the Se-MAD phasing of hSET8 yielded unambiguous electron density for residues 16-24 in histone H4. The H4 peptide binds in a deep cleft formed by the β6-strand and iSET α2-helix on one side and the loop connecting the β 12-strand and the cSET α 3-helix on the other. To facilitate the discussion of histone H4 recognition by hSET8, the analysis of its binding is divided into three categories based on (1) interactions with the H4 peptide backbone, (2) contacts with the side chains of residues N-terminal to Lys-20 in H4, and (3) side-chain interactions with residues C-terminal to Lys-20. The peptide backbone of histone H4 is anchored in the substrate-binding cleft through the formation of a parallel β -sheet with the β 6 -strand (FIG. 3A) and hydrogen-bonds with the side chains of Gln-276, Asp-338, and His-347. Lys-20 is at the center of this β -sheet interaction, which firmly deposits the lysine side chain into the active site. A comparison of the hSET8:histone H4 complex with the structures of DIM-5 (Zhang et al., Mol. Cell 12: 177-185, 2003) and hSET7/9 (Xiao et al., Nature 421: 652-656, 2003a) bound to histone H3 reveals that the parallel β-sheet-binding mode is conserved among the three PKMTs, although the substrate-binding cleft of hSET8 is deeper and more pronounced than in the other enzymes.

To probe the interactions between hSET8 and the H4 backbone, Asp-338 and His-347 were mutated and the effect on histone binding and methylation was assayed. Substitution of Asp-338 to asparagine and alanine in hSET8 abolishes both histone H4 binding and methylation. The carboxylate of Asp-338 also hydrogen-bonds to the amide of Ser-340 in the cSET region, indicating that this residue forms a hydrogen-bond bridge between this serine and Arg-19 in H4 that cannot be maintained in the D338N mutant. Mutation of His-347 to alanine, glutamate, or phenylalanine has variable effects on the affinity and methylation of histone H4. The glutamate and alanine substitutions weaken the interactions between H4 and hSET8 as determined by ITC and also reduce the substrate specificity by approximately fivefold. In contrast, the H347F mutation enhances the affinity of hSET8 for histone H4 as judged by the decrease in the KD and KM values versus the wild-type enzyme, despite the loss of hydrogen bonding between the imidazole $N_\epsilon 2$ atom and the backbone carbonyl of Lys-16 in H4.

The side chains of the residues in the N-terminal part of the histone H4 peptide are recognized through an intimate series of hydrogen-bond, salt-bridge, and van der Waals interactions in the substrate-binding cleft of hSET8. The side chain of Arg-17 in histone H4 engages in a complex array of hydrogen bonding within the binding cleft of the enzyme. The guanidinium group hydrogen-bonds to the carbonyl oxygen of Gly-269 and forms water-mediated hydrogen bonds with the backbone amide of Tyr-271 and the carbonyl oxygens of Tyr-262 and His-18 in H4. Moreover, the Arg-17 guanidinium moiety engages in a salt-bridge interaction with the carboxylate of Glu-259 and also participates in van der Waals contacts with the sulthydryl group of Cys-270. The side chain of His-18 in histone H4 is also involved in a variety of interactions within the substrate binding cleft. In addition to hydrogen bonding to the ribose 3'-OH of AdoHcy, the imidazole group forms edge to-face aromatic ring interactions with the side chains of His-347 and Trp-349 in the cSET region and also participates in van der Waals contacts with the sulfhydryl group of Cys-270. The guanidinium group of Arg-19 in H4 engages in a salt-bridge interaction with the carboxylate of Glu-259 and also forms a cation-π interaction with the phenol side chain of Tyr-274. Collectively, these interactions can be grouped into two categories that appear to be important for recognition of the histone H4 N terminus by hSET8: (1) an edge-to-face aromatic cluster comprised of His-347 and Trp-349 in the enzyme and His-18 in H4 and (2) a salt-bridge network between Arg-17 and Arg-19 in H4 that is bridged by the carboxylate of Glu-259.

To elucidate the determinants of the histone lysine specificity of hSET8, a series of site-directed mutants in the substrate-binding cleft and the N terminus of histone H4 were screened. As mentioned above, mutation of the His-347 to phenylalanine in hSET8 markedly increases affinity for histone H4 by approximately 30-fold. This residue participates in the aromatic cluster with Trp-349 and His-18 in H4, and the H347F mutant substantially enhances the edge-to-face interactions among these aromatic residues. In contrast, an alanine mutation of Cys-270, whose sulfhydryl group engages in van der Waals contacts with the imidazole group of His-18 and the guanidinium moiety of Arg-17, severely disrupts histone H4 binding and methylation. Although this residue does not directly participate in the aromatic cluster or Glu-259 salt bridge, it may serve to orient the side chains of Arg-17 and His-18 within the substrate-binding cleft. In addition to the hSET8 mutations, His-18 in histone H4 was mutated to determine its effect on the specificity of the enzyme. The substitution of His-18 by phenylalanine does not impact the affinity to nearly the same extent as the H347F substitution in the substrate binding cleft. Mutation of His-18 to alanine completely abolishes both histone H4 binding and methylation by hSET8, while a glutamate substitution at this position reduces the kcat/KM value approximately 12-fold. His-18 hydrogen-bonds to the ribose moiety of the cofactor, enhancing the binding of AdoMet during histone methylation. Similarly, the indole ring of Trp-349 not only participates in the edge-to face contacts within the aromatic cluster but also engages in a π-stacking interaction with the adenine ring of the cofactor. Collectively, these interactions underscore the fundamental function of the aromatic cluster in both histone H4 and AdoMet binding.

The salt-bridge network comprised of Glu-259 in hSET8 and Arg-17 and Arg-19 in histone H4 also plays a key role in substrate recognition. An alanine mutation of Glu-259, which resides in the iSET α-helix of hSET8, eliminates this salt-bridge network and dramatically impairs histone H4 binding, emphasizing its importance in substrate specificity. An E259Q substitution modestly reduces histone H4 binding and methylation by hSET8, indicating that hydrogen bonding between this mutant's amide side chain and the H4 arginines can partially compensate for the loss of the ionic interactions in the salt-bridge network. To identify if Arg-17 or Arg-19 (or both) is required for histone H4 recognition by the enzyme, each of these residues was mutated to alanine, glutamate, glutamine, or lysine, respectively. Mutation of Arg-17 to alanine or glutamate completely abolishes histone H4 binding and methylation, while the lysine and glutamine substitutions retain residual activity as substrates. The results with the R17K H4 mutant were somewhat surprising because of the conservation of the positive charge, which can maintain a salt bridge with the carboxylate of Glu-259. Collectively, the Arg-17 mutations indicate that its guanidinium group is specifically recognized through the salt-bridge interaction with Glu-259 and by direct and water-mediated hydrogen bonds within the substrate-binding cleft of hSET8. Whereas the Arg-17 mutants abrogate interactions between the enzyme and histone H4, substitutions of Arg-19 have little impact on either H4 binding or methylation, with the exception of the R19E mutant, which reduces affinity for the enzyme due to its negatively charged carboxylate group. To summarize, the results reveal that the salt bridge formed between Glu-259 in hSET8 and Arg-17 in histone H4 is a prerequisite for substrate binding and methylation of Lys-20 by hSET8.

In contrast to the N-terminal part of histone H4, most of the residues C-terminal to Lys-20 are solvent-exposed and do not engage in significant interactions with hSET8. For example, mutations of Val-21 in H4 to alanine or phenylalanine have only modest effects on substrate binding and methylation by the enzyme. However, substitution of the neighboring Leu-22 by alanine virtually abolishes histone H4 binding and reduces the substrate specificity of the enzyme >50-fold. An inspection of the substrate-binding cleft reveals that this leucine binds in a shallow hydrophobic pocket formed by the aliphatic side chains of Thr-307, Leu-309, and Leu-318 in hSET8. Mutation of Leu-22 to a phenylalanine is readily accommodated in this position, indicating that this hydrophobic pocket is a key determinant in histone H4 recognition. The side chains of the remaining residues in the H4 peptide, Arg-23 and Asp-24, do not engage in extensive interactions within the substrate-binding cleft of the enzyme. To illustrate this, substitution of Arg-23 by alanine or glutamate has no significant effect on H4 binding and methylation. An R23L mutation results in an approximately 10-fold increase in the affinity of hSET8 for histone H4, as judged by its KD and KM values.

Based on the collective biochemical and structural analyses of the histone H4 specificity of hSET8, a consensus motif for substrate recognition by this PKMT was identified: R-$\Omega$-$\zeta$-K-X-$\Phi$ (where $\Omega$ is an aromatic residue, $\zeta$ is a nonacidic residue, K is the methylation site, X is any residue, and $\Phi$ is a bulky hydrophobic residue) (Aasland et al., FEBS Lett. 513: 141-144, 2002). The arginine (R) and an aromatic residue ($\Omega$) are required in the N terminus of this motif because they engage in highly specific interactions within the salt-bridge network and aromatic cluster, respectively. The methylation site K is preceded by any nonacidic residue ($\zeta$), ideally a basic amino acid that can participate in a salt-bridge interaction with Glu-259 in the substrate binding cleft. At the C terminus of the motif, a bulky hydrophobic residue ($\Omega$) is recognized through its binding in the hydrophobic specificity pocket of the substrate-binding cleft.

A comparison of the hSET8:histone H4 complex with the histone H3-bound structures hSET7/9 and DIM-5 (which methylate Lys-4 and Lys-9 in H3, respectively) reveals substantial differences in substrate recognition by these PKMTs. In the crystal structure of DIM-5 bound to histone H3 (Zhang et al., Mol. Cell 12: 177-185, 2003), the enzyme forms an extended parallel β-sheet with the peptide backbone of H3, similar to the hSET8:histone H4 complex. However, the side chains of histone H3 participate in few contacts within the substrate-binding cleft of DIM-5, unlike the intimate series of interactions that are critical for histone H4 recognition by hSET8. Recent studies of the substrate specificity of hSET7/9 have revealed that it recognizes a consensus motif in its protein substrates: K/RS/T-K (in which K is the methylation site) (Chuikov et al., Nature 432: 353-360, 2004). Although hSET7/9 recognizes a specific series of residues preceding its methylation site, this PKMT does not form an extensive β-sheet with the protein substrate, unlike DIM-5 and hSET8. To summarize, the histone specificity of hSET8 appears to be a combination of the substrate-binding modes of DIM-5 and hSET7/9 in which the enzyme not only engages in an extended parallel β-sheet with H4, but also recognizes the residues flanking Lys-20 through an extensive network of sidechain interactions.

Product Specificity of hSET8

Analyses of histone H4 Lys-20 methylation patterns in *Drosophila* and HeLa cells suggest that hSET8 functions as a monomethylase. However, the degree of methylation of Lys-20 catalyzed by this enzyme, commonly referred to as the product specificity of a PKMT (Zhang et al., 2003, supra), has not been rigorously established. To determine the product specificity of hSET8, histone methyltransferase assays and subjected aliquots of the reaction to MALDI mass spectrometry to determine the methylation state of Lys-20 in histone H4 were performed. The data indicate a shift in the mass/charge (m/z) ratio from 1320 to 1334 in the H4 peptide after its reaction with hSET8, corresponding to the addition of a single methyl group. Incubation of the enzyme with the H4 peptide for 24 h results in a complete conversion to monomethyl-Lys-20 with no discernible accumulation of the di- or trimethylated states. Thus, wild-type hSET8 is a bona fide histone H4 Lys-20 monomethylase, correlating with its in vivo function in maintaining Lys-20 monomethylation during cell division.

Examination of the active site reveals two residues, Tyr-245 and Tyr-334, that hydrogen-bond to the ε-amino group of Lys-20 through direct and water-mediated interactions, respectively. The positions of the hydroxyl groups of these tyrosines are structurally conserved with Tyr-245 and Tyr-305, respectively, in the active site of hSET7/9. The Tyr-245/Tyr-305 pair hydrogen-bonds to the ε -amino group of Lys-4 in histone H3 and arrests catalysis at the monomethylation state through stabilization of the methyllysine product complex in hSET7/9 (Xiao et al., 2003a, supra; Zhang et al., 2003, supra). The structural similarities of the lysine-binding channels of these two PKMTs provide a mechanistic explanation for the product specificity of hSET8. To further probe the methyltransfer properties of the enzyme, its active site was superimposed with DIM-5, a histone H3 Lys-9-specific methyltransferase. The alignment reveals that Tyr-245 in hSET8 is structurally conserved with Tyr-178 in DIM-5, whereas Tyr-334 aligns with a phenylalanine (Phe-281), respectively. The absence of a second hydrogen-bonding tyrosine in the active site of DIM-5 enables this PKMT to catalyze trimethylation of Lys-9 in H3 (Zhang et al., 2003, supra). Based on this observation, it was hypothesized that mutation of either Tyr-245 or Tyr-334 in the active site of hSET8 might convert the product specificity of this PKMT to either a Lys-20 di- or trimethylase.

To test this hypothesis, each of these tyrosines was mutated to alanine or phenylalanine, respectively, and the enzymatic activity and product specificity of each mutant were determined. Mutation of Tyr-334 to phenylalanine has virtually no effect on histone H4 binding or methylation by hSET8, whereas an alanine substitution at this position severely compromises enzymatic activity. Mass spectrometric analysis of the Y334F mutant reveals that it is capable of catalyzing mono- and dimethylation of Lys-20 in histone H4. Reaction of the H4 peptide with the Y334F mutant for 24 h primarily yields dimethyl-Lys-20 with no detectable trimethylation of this residue. These results are consistent with the active-site alignment with DIM-5 and also agree with the structurally homologous Y305F mutation in hSET7/9, which converts this PKMT to a histone H3 Lys-4 dimethylase (Zhang et al., 2003, supra). In contrast, mutation of Tyr-245 to either alanine or phenylalanine completely abolishes methyltransfer by hSET8. The effects of these substitutions correlate with mutations of the structurally conserved Tyr-245 in hSET7/9 that disrupt the activity of this PKMT (Xiao et al., 2003a, supra). Taken together, the mutational analysis of Tyr-245 and Tyr-334 in the active site of hSET8 provides a molecular basis for histone H4 Lys-20 monomethylation by this PKMT. The results concur with the Phe/Tyr switch model recently proposed by Cheng and colleagues in which the presence or absence of specific tyrosines within the lysine-binding channel governs the product specificity of SET-domain PKMTs (Collins et al., J. Biol. Chem. 280: 5563-5570, 2005).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

---

---

We claim:

1. A method of measuring the concentration of homocysteine hydrolyzed by a S-adenosylhomocysteine hydrolase enzyme, comprising:
   a) contacting S-adenosylhomocysteine with an S-adenosylhomocysteine hydrolase enzyme, wherein said S-adenosylhomocysteine hydrolase enzyme is S. solfataricus S-adenosylhomocysteine hydrolase and a thiol sensitive fluorophore under conditions such that said S-adenosylhomocysteine hydrolase hydrolyzes said S-adenosylhomocysteine to homocysteine;
   b) contacting said homocysteine with said thiol sensitive fluorophore under conditions such that said thiol sensitive fluorophore is covalently conjugated to said homocysteine to form a labeled homocysteine; and
   c) measuring the level of fluorescence from said labeled homocysteine; wherein said level of fluorescence is correlated with the concentration of said labeled homocysteine.

2. The method of claim 1, wherein said thiol sensitive fluorophore is 10-(2,5-dihydro-2,5-dioxo-1H-pyrrol-1-yl)-9-methoxy-3-oxo-, methyl ester 3H-naphthol(2,1-b)pyran-S-carboxylic acid.

3. The method of claim 1, wherein said S-adenosyl-homocysteine is the product of a S-adenosylmethionine (AdoMet)-dependent methyltransferase reaction.

4. The method of claim 3, wherein said S-adenosylmethionine (AdoMet)-dependent methyltransferase enzyme is a histone methyl transferase.

5. A method of measuring the concentration of homocysteine hydrolyzed by a S-adenosylhomocysteine hydrolase enzyme, comprising:
   a) contacting a S-adenosylmethionine (AdoMet)-dependent methyltransferase enzyme with a substrate for said S-adenosylmethionine (AdoMet)-dependent methyltransferase enzyme under conditions such that S-adenosyl-homocysteine is generated by said S-adenosylmethionine (AdoMet)-dependent methyltransferase enzyme;
   b) contacting said S-adenosyl-homocysteine with a S-adenosylhomocysteine hydrolase enzyme, wherein said S-adenosylhomocysteine hydrolase enzyme is S. solfataricus S-adenosylhomocysteine hydrolase under conditions such that said S-adenosylhomocysteine hydrolase hydrolyzes said S-adenosylhomocysteine to homocysteine;
   c) contacting said homocysteine with said thiol sensitive fluorophore under conditions such that said thiol sensitive fluorophore is covalently conjugated to said homocysteine to form a labeled homocysteine; and
   d) measuring the level of fluorescence from said labeled homocysteine; wherein said level of fluorescence is correlated with the concentration of said labeled homocysteine.

6. The method of claim 5, wherein said S-adenosylmethionine (AdoMet)-dependent methyltransferase enzyme is a histone methyl transferase enzyme.

7. The method of claim 5, further comprising contacting said S-adenosylmethionine (AdoMet)-dependent methyltransferase enzyme and said substrate with a test compound.

8. The method of claim 7, wherein said concentration of labeled homocysteine is altered in the presence of said test compound relative to the level in the absence of said test compound.

9. The method of claim 7, wherein said test compound is a drug.

10. The method of claim 5, wherein said method is a high throughput screening method.

11. The method of claim 5, wherein said thiol sensitive fluorophore is 10-(2,5-dihydro-2,5-dioxo-1H-pyrrol-1-yl)-9-methoxy-3-oxo-, methyl ester 3H-naphthol(2,1-b)pyran-S-carboxylic acid.

12. A method of measuring the concentration of homocysteine hydrolyzed by a S-adenosylhomocysteine hydrolase enzyme, comprising:

a) contacting S-adenosylhomocysteine with an S-adenosylhomocysteine hydrolase enzyme, wherein said S-adenosylhomocysteine hydrolase enzyme is *S. solfataricus* S-adenosylhomocysteine hydrolase and a reporter molecule, wherein said reporter molecule is selected from the group consisting of a fluorescent imaging agent, a chemoluminescent agent, a bioluminescent imaging agent, a radioisotope imaging agent, a phosphorescent imaging agent, and a colorimetric imaging agent under conditions such that said S-adenosylhomocysteine hydrolase hydrolyzes said S-adenosylhomocysteine to homocysteine;

b) contacting said homocysteine with said reporter molecule under conditions such that said reporter molecule is covalently conjugated to said homocysteine to form a labeled homocysteine; and c) measuring the level of fluorescence from said labeled homocysteine;

wherein said level of fluorescence is correlated with the concentration of said labeled homocysteine.

13. The method of claim 12, wherein said S-adenosylhomocysteine is the product of a S-adenosylmethionine (AdoMet)-dependent methyltransferase reaction, and wherein said S-adenosylmethionine (AdoMet)-dependent methyltransferase enzyme is a histone methyl transferase.

* * * * *

SEQUENCE LISTING

```
<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Methylation site of CLR4
<220> FEATURE:
<221> NAME/KEY: MISC_FEATURE
<222> LOCATION: (9)..(9)
<223> OTHER INFORMATION: Methylation site of CLR4
<220> FEATURE:
<221> NAME/KEY: MISC_FEATURE
<222> LOCATION: (14)..(14)
<223> OTHER INFORMATION: Methylation site of CLR4

<400> SEQUENCE: 1

Ala Arg Thr Lys Gln Thr Ala Arg Lys Ser Thr Gly Gly Lys Ala
1               5                   10                  15
```